United States Patent [19]

Shen

[11] 4,094,663
[45] June 13, 1978

[54] QUADRICYCLIC MORPHOLINOBENZIMIDAZOLE COMPOUNDS

[75] Inventor: Kelvin Kei-Wei Shen, Fountain Valley, Calif.

[73] Assignee: United States Borax & Chemical Corporation, Los Angeles, Calif.

[21] Appl. No.: 832,137

[22] Filed: Sep. 12, 1977

[51] Int. Cl.$^2$ .................. C07D 498/04; A01N 9/22
[52] U.S. Cl. ........................................ 71/92; 544/99; 544/166; 544/177
[58] Field of Search ........................ 544/99; 71/92

[56] References Cited

U.S. PATENT DOCUMENTS 4,049,422  9/1977  Shen ............................................. 71/92

Primary Examiner—Alan L. Rotman
Assistant Examiner—R. W. Ramsuer
Attorney, Agent, or Firm—James R. Thornton

[57] ABSTRACT

Quadricyclic morpholinobenzimidazole compound having a trimethylene group on the aromatic ring and the N-oxide derivative thereof. The compounds are useful as herbicides.

10 Claims, No Drawings

4,094,663

QUADRICYCLIC MORPHOLINOBENZIMIDAZOLE COMPOUNDS

This invention relates to a novel quadricyclic morpholinobenzimidazole and its N-oxide derivative which can be used as herbicides, especially as post-emergence herbicides.

RELATED APPLICATIONS

Shen et al. co-pending applications, Ser. No. 671,452 filed Mar. 29, 1976 now U.S. Pat. No. 4,049,422 and Ser. No. 776,395 filed Mar. 10, 1977, disclose certain tricyclic morpholinobenzimidazole compounds and the N-oxide derivatives thereof which are useful as herbicides.

BACKGROUND OF THE INVENTION

Nair and Adams, *Journal of the American Chemical Society*, Volume 33, pages 3518–3521 (1961) describe the preparation of certain tricyclic morpholinobenzimidazole compounds optionally having a chloro, methyl or nitro substituent at the 5-position. Fielden, et al., *Journal of the Chemical Society*, No. 7, pages 696–701 (1973) report the preparation of tricyclic morpholinobenzimidazole N-oxide and its 5-nitro derivative by cyclization of the corresponding ortho-nitrophenylmorpholine compound.

SUMMARY OF THE INVENTION

This invention provides a novel quadricyclic morpholinobenzimidazole compound of the formula:

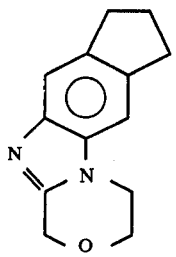

and the N-oxide derivative thereof. Such compounds are useful as herbicides, especially as post-emergence herbicides.

The morpholinobenzimidazole can be prepared according to the following synthetic route:

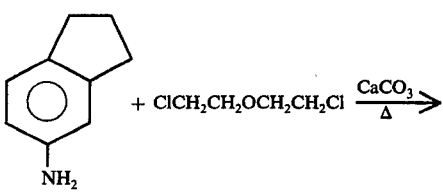

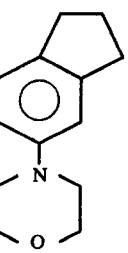

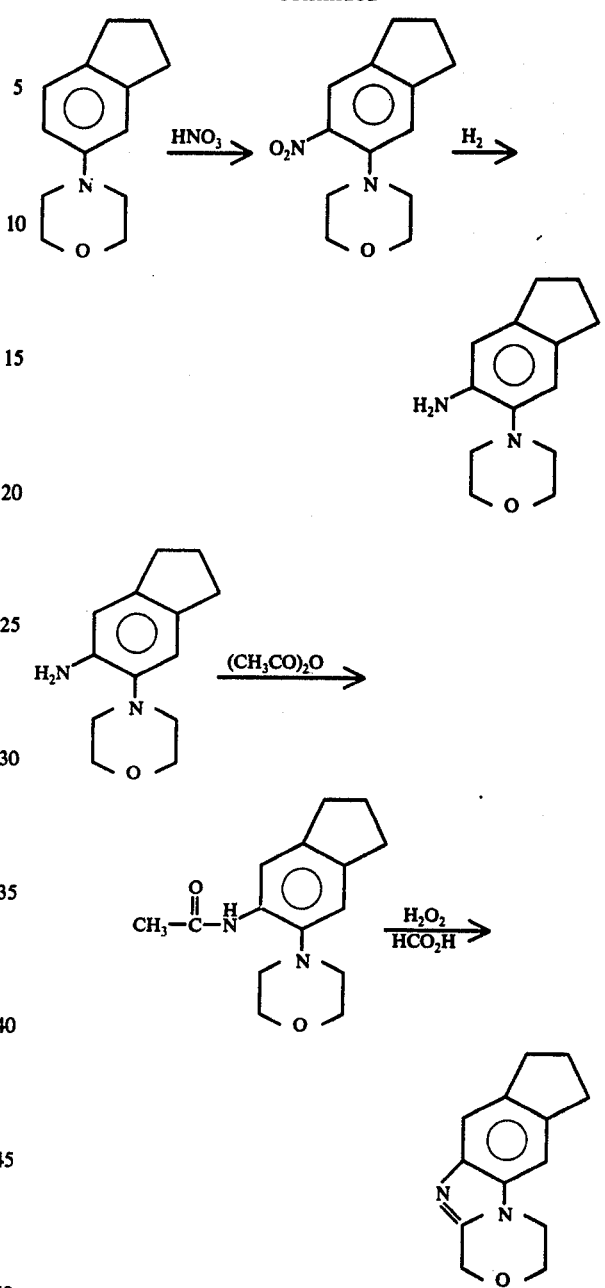

Such reactions are typical organic synthesis reactions well known to organic chemists. The synthesis is illustrated by the following examples:

EXAMPLE I

4-(3,4-trimethylenephenyl)morpholine

An autoclave was charged with 50 g. (0.38 mol) of 5-aminoindane, 55 g. (0.38 mol) of bis-(2-chloroethyl)ether, 38 g. (0.38 mol) of calcium carbonate, 0.2 g. of benzyltriethylammonium chloride, 50 ml. of tetrahydrofuran and 50 ml. of water. The mixture was heated at 150° C. for 96 hours. The carbon dioxide was slowly vented and the resultant solution was poured into 150 ml. of water. The mixture was extracted twice with 100 ml. of diethyl ether. The combined ether extracts were dried over anhydrous sodium sulfate, concentrated and distilled under reduced pressure to give 62 g. (80% yield) of 4-(3,4-trimethylenephenyl)morpholine, b. p. 150° C./1.2 mm.

EXAMPLE II 4-(2-nitro-4,5-trimethylenephenyl)morpholine 4-(3,4-trimethylenephenyl)morpholine was nitrated by reaction with 90% nitric acid in the presence of a 1:1 mixture of acetic acid and sulfuric acid. The product was isolated as a dark, viscous oil by extraction with methylene dichloride from a neutralized ice-water mixture. Purification by use of a silica gel column eluted with methylene chloride gave the crystalline product, m. p. 50°–50.5° C.

EXAMPLE III 4-(2-amino-4,5-trimethylenephenyl)morpholine

The nitromorpholinobenzene compound prepared as described in Example II was reduced with hydrogen over a palladiumcarbon catalyst to give the corresponding amino derivative, m. p. 89°–90.5° C.

EXAMPLE IV 4-(2-acetamido-4,5-trimethylenephenyl)morpholine

The 2-aminomorpholine compound prepared as described in Example III was acetylated with acetic anhydride in dimethoxyethane to give the N-acetyl derivative, m.p. 98° C.

EXAMPLE V 5,6-trimethylene-1,2-(gamma-oxatetramethylene)benzimidazole

The N-acetyl derivative prepared according to Example IV (2.14 g.) was dissolved in 12.8 ml. of 88% formic acid, and 6.4 ml of 30% hydrogen peroxide was added drop-wise to the reaction mixture at boiling temperature over a period of about 20 minutes. The resultant mixture was heated at reflux temperature for an additional 2 hours, allowed to cool and then poured into a water-ice mixture. After neutralization of the water solution with ammonium hydroxide, the product precipitated as light tan crystals. Isolation by filtration and air drying gave 1.4 g. (79% yield) of the desired product, m. p. 197° C.

The corresponding N-oxide derivative can be prepared by reaction of the substituted ortho-nitrophenylmorpholine with refluxing hydrochloric acid according to the following equation:

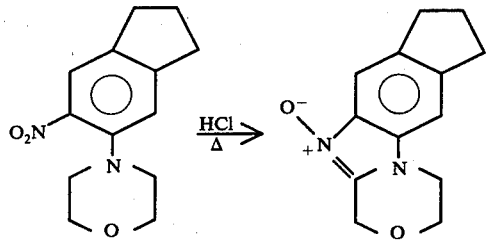

Example VI illustrates the reaction.

EXAMPLE VI 5,6-trimethylene-1,2-(gamma-oxatetramethylene)benzimidazole N-oxide 4-(2-Nitro-4,5-trimethylenephenyl)morpholine (28.0 g.; 113 mmol.) was added to 180 ml. of 20.2% hydrochloric acid and the solution heated at 110° C. for 24 hours. The reaction mixture was then concentrated under reduced pressure, neutralized with sodium carbonate and filtered to collect the crude crystalline product. The crude product was dissolved in a 3:1 mixture of methylene chloride and methanol and passed through a 4 × 30 cm. silica gel column, eluted with a 9:1 mixture of methylene chloride and methanol. The 3rd to 5th 100 ml. fractions gave 2.0 g. (8%) of the N-oxide as the hydrate ($2H_2O$), m. p. 147° C.

The compounds of this invention are useful as herbicides and are especially useful as selective post-emergence herbicides for controlling weeds in crops such as corn, rice and wheat. Application rates in the range of from about 0.5 to 10 pounds per acre of the active compounds are generally effective in controlling weed growth, especially the broadleaf weeds such as morningglory, jimsonweed, lambsquarter and velvetleaf.

EXAMPLE VII

In a greenhouse test, 5,6-trimethylene-1,2-(gamma-oxatetramethylene)benzimidazole was applied at rates of one and two pounds per acre to a wide variety of crops and weeds planted in flats. The compound was sprayed, as an ethanol solution, onto the plants when they were about one inch in height. The flats were kept in the greenhouse and watered when needed. Twenty-one days after treatment, the flats were examined and the plants rated for herbicidal activity according to the following scale. The results are given in Table I. Where two numbers are shown; i.e., 8/4, the first number represents the percentage of "kill" and the second number is the "injury" rating for the remaining plants.

0 = no effect

1 = < 10% injury

2 = 10–40% injury

3 = 40–70% injury

4 = > 70% injury

5 = < 25% kill

6 = 25–50% kill

7 = 50–75% kill

8 = 75–99% kill

9 = complete kill

TABLE I

| Plant Specie | Activity 1 lb./A. | 2 lb./A. |
|---|---|---|
| corn | 0 | 0 |
| cotton | 0/3 | 7/4 |
| dry beans | 9 | 9 |
| peanuts | 0 | 0/1 |
| rice | 0 | 0/1 |
| soybeams | 0/3 | 5/4 |
| wheat | 0 | 0 |
| alfalfa | 8/0 | 8/0 |
| cocklebur | 0/2 | 5/3 |
| jimsonweed | 8/1 | 8/1 |
| lambsquarters | 8/1 | 8/2 |
| morningglory | 9 | 6/0 |
| mustard | 5/1 | 7/0 |
| prickly sida | 5/1 | 5/1 |
| pigweed | 7/2 | 8/2 |
| sesbania | 6/1 | 9 |
| velvetleaf | 8/0 | 8/0 |
| ragweed | 5/2 | 8/4 |
| nightshade | 0/1 | 5/2 |
| barnyardgrass | 0 | 0 |

TABLE I-continued

| Plant Specie | Activity 1 lb./A. | 2 lb./A. |
|---|---|---|
| foxtail | 0 | 0 |
| Johnsongrass | 0 | 0 |
| wild oats | 0 | 5/0 |

EXAMPLE VIII 5,6-Trimethylene-1,2-(gamma-oxatetramethylene)-benzimidazole N-oxide was applied at a rate of 5 pounds per acre to soybeans (SB), velvetleaf (VL), oats (O) and millet (M). The compound was sprayed, as an ethanol solution, onto the plants when they were about 1 inch in height. The treated plants were kept in the greenhouse and watered when needed. Fourteen days after treatment, the plants were rated for herbicidal activity according to the scale set forth in Example VII. The results are given in Table II.

TABLE II

| HERBICIDAL ACTIVITY | | | |
|---|---|---|---|
| SB | VL | O | M |
| 3 | 9 | 2 | 1 |

Since a relatively small amount of one or more of the active compounds should be uniformly distributed over the area to be treated, they preferably are formulated with conventional herbicide carriers, either liquid or solid. Thus, the compounds can be impregnated on or admixed with a pulverulent solid carrier such as lime, talc, clay, Bentonite, calcium chloride, vermiculite and the like. Alternatively, they can be dissolved or suspended in a liquid carrier such as water, kerosene, alcohols, diesel oil, mineral oil, xylene, benzene, glycols, ketones, and the like. Since the compounds will form water-soluble salts such as with mineral acids, they can be formulated with water.

A surfactant is preferably included to aid in dispersion, emulsification and coverage. The surfactant can be ionic or non-ionic and may be liquid or solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkyl-sulfonic acids, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers which are miscible with the active agent or other liquids in which the compound may be suspended or dispersed, can be used. A surfactant is also generally included to facilitate such dilution or dispersion in water. However, the surfactant itself may comprise the carrier in such concentrates.

Various changes and modifications of the invention can be made, and, to the extent that such variations incorporate the spirit of this invention, they are intended to be included within the scope of the appended claims.

What is claimed is:

1. A compound of the formula

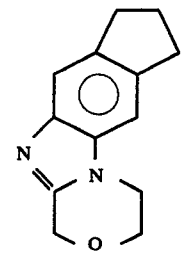

and the N-oxide derivative thereof.

2. The compound according to claim 1, 5,6-trimethylene-1,2-(gamma-oxatetramethylene)benzimidazole.

3. The compound according to claim 1, 5,6-trimethylene-1,2-(gamma-oxatetramethylene)benzimidazole N-oxide.

4. An herbicidal composition comprising an herbicidally effective amount of a compound of the formula according to claim 1 and an inert carrier therefor.

5. An herbicidal composition according to claim 4 in which a surfactant is included.

6. The method for controlling weed growth which comprises applying to the locus of said weeds a phytotoxic amount of a compound according to claim 1.

7. The method according to claim 6 in which said compound is applied at a rate of 0.5 to 10 pounds per acre.

8. The method according to claim 6 in which said compound is applied to the foliage of said weeds.

9. The method according to claim 8 in which said weeds are in the presence of a crop selected from corn, rice and wheat.

10. The method according to claim 6 in which said compound is 5,6-trimethylene-1,2-(gamma-oxatetramethylene)benzimidazole.

* * * * *